United States Patent
Li

(10) Patent No.: US 6,716,174 B1
(45) Date of Patent: Apr. 6, 2004

(54) FLEXIBLE GEOMETRY FOR REAL-TIME ULTRASOUND VOLUME IMAGING

(75) Inventor: Xiang-Ning Li, Mill Creek, WA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/259,705

(22) Filed: Sep. 27, 2002

(51) Int. Cl.[7] .................................................. A61B 8/02
(52) U.S. Cl. ...................................................... 600/447
(58) Field of Search .................................. 600/437, 447, 600/443, 459, 460, 444; 73/625, 626, 628

(56) References Cited

U.S. PATENT DOCUMENTS

| | | | |
|---|---|---|---|
| 1,636,510 A | | 7/1927 | Hayes et al. |
| 5,181,514 A | | 1/1993 | Solomon et al. |
| 5,229,933 A | * | 7/1993 | Larson, III ................. 600/459 |
| 5,320,104 A | | 6/1994 | Fearnside et al. |
| 5,546,807 A | | 8/1996 | Oxaal et al. |
| 5,617,863 A | | 4/1997 | Roundhill et al. |
| 6,013,032 A | * | 1/2000 | Savord ....................... 600/443 |
| 6,224,552 B1 | | 5/2001 | Jago et al. |
| 6,241,675 B1 | | 6/2001 | Smith et al. |
| 6,276,211 B1 | * | 8/2001 | Smith .......................... 73/626 |
| 6,375,617 B1 | * | 4/2002 | Fraser ........................ 600/443 |
| 6,419,633 B1 | * | 7/2002 | Robinson et al. ........... 600/443 |
| 6,491,632 B1 | * | 12/2002 | Taylor ........................ 600/443 |
| 6,497,663 B2 | * | 12/2002 | Fraser et al. ................ 600/443 |

OTHER PUBLICATIONS

"3-D Ultrasound Imaging: A Review" IEEE Engineering in Medicine and Biology, Nov./Dec. 1996, pp. 41–49.

* cited by examiner

Primary Examiner—Dennis W. Ruhl
Assistant Examiner—Ruby Jain
(74) Attorney, Agent, or Firm—John Vodopia

(57) ABSTRACT

An ultrasonic imaging method and apparatus are described for electronically scanning a volumetric region using a two dimensional array of transducer elements coupled to a beamformer. Elements of the array are actuated to transmit ultrasonic energy into the volumetric region. Echo signals are received by elements of the array in response to the transmitted ultrasonic energy. Beams are formed which sample the volumetric region that allows choices of size, location and geometry shapes such as in one of a circular and elliptical beam pattern.

18 Claims, 14 Drawing Sheets

FLEXIBLE GEOMETRY FOR REAL-TIME ULTRASOUND VOLUME IMAGING

BACKGROUND

This invention relates to ultrasonic diagnostic imaging systems and, in particular, to increasing the volume or frame rate of volume acquisition in ultrasonic diagnostic imaging systems for applications in volume imaging.

The image quality of medical ultrasound has made it indispensable in diagnosis and management of many diseases. To that end, the development of 3-D ultrasound imaging, for example, 3-D, B-mode, color Doppler and power Doppler, as applied to acquisition, reconstruction and rendering techniques is moving ahead quite steadily with valuable results to the field of diagnostic imaging.

One of the goals of 3-D ultrasound imaging, as stated by Aaron Fenster and Donal B. Downey, 3-D *Ultrasound Imaging: A Review*, IEEE ENGINEERING IN MEDICINE AND BIOLOGY, pages 41–49, November–December 1996, is to reduce to variability of conventional acquisition techniques in order to allow ultrasound diagnosticians an ability to better view patient organs in 3-D. Fenster and Downey support the position of the inventors herein that the relative position and angulation (acquisition geometry) must be accurately known to avoid geometric distortion, and artifacts and distortion due to respiratory, cardiac and involuntary motion. The latter requires rapid and appropriately gated acquisition. To this end, the present invention focuses on electronic 2-D scanning, using a 2-D transducer array.

FIG. 1 illustrates an ultrasonic diagnostic imaging system which may be used in accordance with the principles of the present invention. A scanhead (or transducer, as used interchangeably herein) 26, including a transducer array 10, is connected by a cable 11 to a beamformer 36. The beamformer 36 controls the timing of actuation signals applied to the elements of the transducer array 10 for the transmission of steered and focused transmit beams, and appropriately delays and combines signals received from the transducer elements to form coherent echo signals along the scanlines delineated by the transmit beams. The timing of the beamformer transmission is also responsive to an electrocardiograph (ECG) signal when it is desired to synchronize or gate image acquisition with a particular phase of the heart cycle. The beamformer 36 is further responsive to a scanhead position signal when the transducer is being mechanically moved to sweep ultrasonic beams over a volumetric region, thereby enabling beams to be transmitted when the transducer is properly oriented with respect to the volumetric region.

The output of the beamformer 36 is coupled to a pulse inversion processor 38 for the separation of fundamental and harmonic frequency signals. Pulse inversion processors are well known in the art and are described in U.S. Pat. Nos. 5,706,819 and 5,951,478. These patents describe how echoes from alternately phased pulses can be used to separate harmonic contrast signals from fundamental signals. The fundamental and/or harmonic signals may be B mode processed or Doppler processed, depending upon the desired information to be displayed. For Doppler processing, the signals are coupled to a wall filter 22 which can distinguish between flow, stationary tissue, and moving tissue. A preferred wall filter for contrast imaging is described in U.S. patent application Ser. No. 09/156,097, which is also capable of performing harmonic contrast signal separation. The filtered signals are applied to a Doppler processor 42, which produces Doppler power, velocity, or variance estimation.

A preferred Doppler processor for harmonic Doppler signal estimation is described in U.S. Pat. No. 6,036,643. Artifacts from scanhead motion which can contaminate Doppler imaging are removed by a flash suppressor 44. Various techniques may be used to remove flash artifacts prior to or subsequent to image formation, including the notch filter technique described in U.S. Pat. No. 5,197,477 and the min-max filter technique described in U.S. Pat. No. 5,782,769. The processed Doppler signals are stored in a Doppler image memory 40'. Signals which are to be B mode processed are applied to a B mode processor 24 which detects the signal amplitude. B mode processed signals are stored in a tissue image memory 40.

The B mode and Doppler signals are applied to a coordinate transformation processor 46. For conventional two dimensional imaging, the coordinate transformation processor will function as a scan converter, converting polar coordinates to Cartesian coordinates as necessary and filling spaces between received lines with interpolated image data. The scan converted images are coupled to a video processor 70 which puts the image information into a video format for display of the images on a display 100. The images are also coupled to a Cineloop® memory 56 for storage in a loop if that function is invoked by the user.

When 3D imaging is being performed by the ultrasound system, the coordinate transformation processor may be used to scan convert the tissue and Doppler signals in planes of image information over the scanned volume, or may be used to transform the coordinates of the image data into a three-dimensional data matrix. Preferably the coordinate transformation processor operates in cooperation with a volume rendering processor 50, which can render a three-dimensional presentation of the image data which has be processed by the coordinate transformation processor.

Three-dimensional images of tissue are rendered in accordance with tissue rendering parameters 54 which are selected by the user through a control panel or user interface (UIF). Three-dimensional images of Doppler information are rendered in accordance with blood flow rendering parameters 52. These parameters control aspects of the rendering process such as the degree of transparency of tissue in the three-dimensional image, so that the viewer can see the vasculature inside the tissue. This capability is important when 3D images of both tissue and flow are being rendered, as described in U.S. Pat. No. 5,720,291. Three-dimensional images can be stored in the Cineloop® memory 56 and replayed to display the scanned volume in a dynamic parallax presentation, for instance. A three-dimensional rendering of flow without the surrounding tissue, as described in U.S. Pat. No. Re. 36,564, can reveal the continuity of flow of blood vessels and obstructions in those vessels and is useful for coronary artery diagnosis in accordance with the present invention.

Different transducers can be used to scan a volumetric region of the heart which includes the coronary arteries Either a 1D array (azimuth steered) or a 1.5D or 1.75D array (azimuth steered and elevation focused) may be moved mechanically to sweep beams over the three-dimensional volume. For electronic steering either a 1.75D array (minimally electronically steered in azimuth and elevation) or a 2D array (fully electronically steered in azimuth and elevation) may be used. An embodiment which uses a 2D transducer array 10" is shown in FIG. 2. An important consideration in the use of two dimensional arrays is the number of cable wires used to connect the probe to the ultrasound system. Various approaches can be used to reduce the number of cable conductors and thus the size of the cable, including wireless links to the ultrasound system, micro-beamforming in the probe, digital or analog time multiplexing, the use of sparse arrays, and the use of transmit/receive multiplexers. One solution is a radio frequency (RF) probe which transmits echo signals wirelessly to the ultrasound system as described in U.S. Pat. No. 6,142,946.

Another solution, when a cable connection is used, is to partition the beamformer between the scanhead and the ultrasound system as described in U.S. Pat. No. 6,102,869. The FIG. 2 example implements this approach wherein elevation beamforming in the transducer 26 and azimuth beamforming in the ultrasound system 101 is performed. For example, suppose that the two dimensional array has 128 columns of elements extending in the azimuth direction (indicated by the AZ arrow in the drawing) and six rows of elements in the elevation direction (indicated by the EL arrow). If each element of the array were connected by its own conductor to the ultrasound system, a cable of 768 signal conductors would be required. FIG. 2 shows that each column of six elements is coupled to an elevation beamformer 36a which appropriately excites (on transmit) and delays and combines (on receive) signals from the six elements of the column. This combines the six signals in each column into one elevation beamformed signal, which is then coupled over a cable conductor to the ultrasound system, where the elevation beamformed signals are beamformed in the azimuth direction. In the foregoing example, the 128 elevation beamformed signals are coupled over the 128 conductors of a cable 11, a significant reduction in cable size as compared to a probe without scanhead beamforming. At least elevation steering is performed in the elevation beamformer 36a, and preferably both steering and focusing are performed in the elevation beamformer.

The operation of the elevation beamformer is illustrated in FIGS. 3a and 3b. In FIG. 3a, a beam is being steered normal to the array transducer as indicated by the 0° arrow extending from the elements $10_1$ through $10_n$, which comprise a column of elements in the elevation direction. Signals at the center of the column are delayed more than signals at the ends of the column as indicated by the relative length of the delays 102 for the different elements to effect a focus. Delayed receive signals are combined by a summer 104, then coupled over a signal lead in the cable 11 to the azimuth beamformer 36b. FIG. 3b illustrates the situation when a beam is to be transmitted or received from the left at a 30° inclination in elevation as indicated by the 30° arrow. In this case signals on the left side of the array are more greatly delayed as indicated by the relative length of the delays 102. Received signals are combined by the summer 104 and coupled through the cable to the azimuth beamformer 36b.

FIGS. 4a–7c illustrate the implementation of the elevation beamformer in three different ways (neglecting any buffering or gain elements). FIG. 4a illustrates an analog implementation in which each transducer element $10_m$ is coupled to an analog delay line 106. The length of the delay is set by choosing the input or output tap of the delay line and the delayed signals are coupled to an analog summer or to an A/D converter if the signals are to be digitally combined. In FIG. 4b, each transducer element $10_m$ is coupled to a charge-coupled device (CCD) delay line 108. The length of the delay is set by choosing an input or output tap that determines the number of charge storage elements in the delay line or by varying the rate at which the charge samples are passed through the charge storage elements. The outputs of the delay lines are summed either in sampled analog format or after being digitized.

FIG. 4c illustrates a digital embodiment of an elevation beamformer. In this example the elevation beamformer has 128 sub-beamformers 120, each processing the signals from one elevation column of six transducer elements. Each of the transducer elements $10_1$ through $10_n$ is coupled to an A/D converter 110 and the digitized signals are delayed by a digital delay line 112, which may be formed by a shift register, FIFO register, or random access memory. The appropriately delayed signals are combined in a summer 104 and coupled over cable conductors to the azimuth beamformer. To conserve cable conductors when using multi-bit signal samples, the data values from several of the beamformer channels 120 can be interleaved (time multiplexed) and sent over the same group of conductors at a data rate sufficient for the desired level of real-time imaging performance.

FIG. 5 illustrates the organization and control of a number of beamformer channels 120 of a scanhead elevation beamformer. The beamformer comprises N elevation sub-beamformers $120_1$–$120_n$ where each sub-beamformer receives signals from a column of transducer elements in the elevation direction, as indicated by the number 6 for this example. Data to control the elevation beamforming (such as elevation angle and focusing) is sent to a timing & delay decoder & data store 126 in the scanhead 26, preferably serially over a cable conductor. This control data is decoded and delay values coupled to a delay control 124, which sets the beamformer channels for the desired delays for each transducer element. For dynamic focusing the delays are changed as echoes are received. The elevation aperture can be varied by applying zero weights to some of the outermost channels when a smaller (near field) aperture is desired. The data received by the timing & delay decoder & data store 126 is also used to control transmit timing by pulse transmitters $122_1$–$122_n$, each of which controls the transmission of the six transducer elements in an elevation column in this example.

When received echo signals are processed in the analog domain as illustrated by FIGS. 4a and 4b, the signals from the 128 channels of the elevation beamformer in this example are sent over 128 cable conductors to the azimuth beamformer 36b. When the echo signals are processed digitally, the signals from the 128 channels are interleaved (time multiplexed) and sent over digital conductors of the cable 11 to the azimuth beamformer in the ultrasound system 101.

A true 2D electronically steered embodiment may be seen in commonly owned and copending U.S. application Ser. No. 09/912,785, incorporated herein by reference in its entirety. The invention therein is illustrated herein as FIG. 6. This drawing shows a plan view of a 2D transducer array 200 of greater than three thousand transducer elements. For ease of illustration, the small boxes in the drawing which represent individual transducer elements are shown spaced apart from each other. However, in a constructed embodiment, the individual transducer elements are closely packed in a repeating hexagonal pattern. The 2D array has an overall dodecahedral outline. In a preferred mode of operation, beams are transmitted outward from the center of the array and can be steered and focused in a cone of at least ±30° about a line normal to the center of the array. When steered straight ahead, echoes received from along a transmitted scanline are initially received at the center of the array and then in circular or arcuate groupings of elements centered on and extending outward along the projection of the scanline onto the surface of the array. In the illustrated embodiment, approximately the central one-quarter of the elements are used for beam transmission. The entire array is available for echo reception.

The array 200 of FIG. 6 is seen to be drawn in alternate light and dark groupings 202 of twelve transducer elements. One of these groupings 202, referred to herein as a "patch" of transducer elements, is shown in a separate enlarged view in FIG. 7. These irregular hexagonal patches 202 of twelve elements are beamformed together during echo reception as discussed in detail below. Elements in the center of the array (approximately 750 elements) are connected in groups of three for transmission by high voltage mux switches.

FIGS. 8a–8f show some of the three-element configurations that are possible during beam transmission. The transmit groupings can also simply be three elements adjacent to each other in a straight line. The exact configuration or configurations used to transmit a given beam depend upon the desired beam characteristics and its azimuth. Four elements may also be connected together for transmission as illustrated by the diamond shaped grouping of four elements in FIG. 8g.

Since a cable with more than three thousand conductors is not currently practical, each patch of twelve elements of the array is beamformed in the scanhead. This reduces the number of signals which must be coupled to the ultrasound system beamformer to approximately 256. Then, a 256 channel beamformer in the ultrasound system can be used to beamform the partially beamformed signals from the scanhead.

Because the elements of each receive patch of twelve elements of the 2D array are sufficiently small, contiguously located, and closely packed, the echo signals received by the elements of a patch will be aligned to within one wavelength at the nominal receive frequency for steering angles of approximately 40° or less (neglecting focal delays). The echoes of the elements are then sampled to bring all of the patch element signals into precise time alignment. The sampling is done with a range of sampling delays with a precision of a fraction of a wavelength to bring the signals from all of the patch elements to a time alignment within the precision of the sampling clock quanta, preferably 1/16 of a wavelength or less.

The time-aligned signals from the patch elements are then combined. This beamforming of each patch is done by microelectronics located immediately behind the transducer array in the scanhead to facilitate interconnections. Sample time shifting and alignment is performed by the sampling delay line shown in FIG. 9. Each element 204 of a patch of elements which is to be partially beamformed is coupled by way of an amplifier 206 to a sampling input switch 208. The sampling input switch 208 is continually conducting samples of the transducer signal onto capacitors 212 in a sequential manner. The sequencing of the switch 208 is under control of a ring counter 210 which is incremented by a clock signal. As the darkened segment of the ring illustrates, the sampling input switch is continually sampling the input signal onto successive ones of the capacitors 212 in a circular manner. The amplifier 206 has a bipolar output drive so that the charge of a capacitor can be either increased or decreased (discharged) to the instantaneous signal level at the time of sampling.

The signal samples stored on the capacitors 212 are sampled by a sampling output switch 214 which samples the stored signals in a sequential manner under control of a second ring counter 216. As shown by the darkened segment on the ring of the second ring counter 216, the sampling output switch 214 samples the stored signals in a particular time relationship to the input switch and its ring counter. The time delay between the input and output sampling is set by a time shifter 220 which establishes the time delay between the two ring counters. Thus, the time of sampling of the output signal samples can be incrementally advanced or delayed as a function of the timing difference between the two ring counters. This operation can be used to bring the output signal samples of all the elements of a patch into a desired time alignment such as the sampling time of a central element of the patch. When the signals from all of the elements of the patch are within a desired range of sampling time, the signals can be combined into one signal for further beamforming in the ultrasound system. The time aligned output signals are further amplified by an amplifier 218 and coupled to a summer for combining with the signals of the other elements of the patch.

Three-dimensional imaging requires that the volumetric region be sufficiently sampled with ultrasound beams over the entire volume. This requires a great many transmit-receive cycles which causes the time needed to acquire a full set of volumetric data to be substantial. The consequences of this substantial acquisition time are that the frame rate of a real-time 3D display will be low and that the images will be subject to motion artifacts. Hence it is desirable to minimize the time required to acquire the necessary scanlines of the volumetric region.

One approach is to employ multiline beamforming, scanline interpolation, or both, as shown in FIGS. 10 and 11. While beams may be steered in a square or rectangular pattern (when viewed in cross-section) to sample the volume being imaged, it is known to acquire data using beams oriented in triangular or hexagonal patterns in the volumetric region to sufficiently and uniformly spatially sample the region being imaged. FIG. 11a is a cross-sectional view through the volumetric region in which scanlines in the volumetric region are axially viewed.

As can be seen in FIGS. 11a and 11b, nineteen scanlines are produced for every transmit beam. The scanline locations are spatially arranged in hexagonal patterns. The nineteen scanline locations of one hexagonal pattern are denoted by circles which represent axial views along the scanlines. The nineteen scanline locations are insonified by a "fat" transmit beam of a desired minimum intensity across the beam. The transmit beam in this example is centered on the location of scanline 270, and maintains the desired acoustic intensity out to a periphery denoted by the dashed circle 250, which is seen to encompass all nineteen scanline locations. The echoes received by the elements of the transducer array are partially beamformed by a microbeamformer 280 in the scanhead as described above and coupled to a 19x multiline beamformer 282 in the ultrasound system as shown in FIG. 10a.

The ultrasound system as shown in FIG. 10a can include a 2D transducer array as shown in FIG. 11a, where the 2D transducer array of 3072 elements is operated in patches of 12 elements, producing 256 patch signals which are coupled to the ultrasound system by a cable 281 with 256 signal conductors without multiplexing. The 19x multiline beamformer 282 processes the 256 echo signals received from the transducer patches with nineteen sets of delays and summers to simultaneously form the nineteen receive scanlines 252–274 shown in FIG. 11a. The nineteen scanlines are coupled to an image processor 284, which performs some or all of the harmonic separation, B mode, Doppler, and volume rendering functions as known in the art. The three-dimensional image is then displayed on the display 100.

Interpolation may be used to form scanline data, either alternatively to or in conjunction with multiline scanline formation. FIG. 11b illustrates a series of scanlines 361–367 marked by the darkened circles which have been acquired from a volume being imaged in a hexagonal pattern as indicated by the background grid pattern. The scanlines 361–367 can be acquired individually or in groups of two or more by multiline acquisition. Scanlines at the undarkened circle locations are interpolated from the acquired scanlines using two-point RF interpolation. The interpolated scanline 371 is interpolated by weighting each of the adjacent scanlines 361 and 362 by ½, then combining the results. The weights used are a function of the location of the scanline being produced in relation to the locations of the three received scanlines whose values are being interpolated.

Similarly, interpolated scanline 372 is interpolated using adjacent scanlines 362 and 367, and interpolated scanline 373 is interpolated using adjacent scanlines 361 and 367. Each group of three scanlines is used to interpolate three intermediate scanlines using weighting factor which are a factor of two ($2^{-1}$), enabling the interpolation to be performed rapidly by shifting and adding the bits of the data being interpolated. This avoids the use of multipliers and multiplication and affords high-speed processing advantageous for real-time 3D display rates.

FIG. 11c illustrates a further iteration of the interpolation of FIG. 11b in which the scanline density of the volume is increased even further by interpolation. In the illustration shown in FIG. 11c, two further sets of scanlines 381–383 and 387–392 are interpolated between the previous set. These scanlines may be interpolated using the previously interpolated set of scanlines, or they may be interpolated directly (and simultaneously, if desired) from the acquired scanlines 361,362,367. These scanlines also have the advantage of being weighted by weighting factors which are a factor of two.

The set of interpolated scanlines most central to the three received scanlines, 381–383, are interpolated using weighting factors of ½ and ¼. Scanline 381, for instance, is produced by (½(scanline 361)+¼(scanline 362)+¼(scanline 367)). The outer set of scanlines is produced by ¼, ¾ weights as described in U.S. Pat. No. 5,940,123. Scanline 392, for instance, is produced by (¼(scanline 367)+¾ (scanline 361)) or, to avoid multiplication, (¼(scanline 367)+¼(scanline 361)+¼(scanline 361)+¼(scanline 361)). FIG. 11c illustrates corresponding sets of interpolated scanlines for received scanlines 362,363,367, including the central group of scanlines 384–386, and the outer set of scanlines 393–396. To reduce motional artifacts, the received scanline data can be filtered in either RF or detected form prior to display.

The above example uses a linear interpolation filter kernel. It is also possible to use an interpolation kernel that has a non-liner shape (such as, for example, cosine, sinc, etc.) However the filter coefficients of these other filters will generally not have the desirable power of two property.

The use of patches to reduce the size of the cable needed to connect the scanhead to the ultrasound system may, under certain operating conditions, give rise to undesired grating lobes in the scanhead's beam pattern. This is due to the grouping of individual transducer elements into a single unit, giving the transducer array a coarser pitch, even with the use of micro-beamforming as described above. This problem can be reduced by considering each patch to be a sub-aperture of the entire 2D array which is capable of receiving signals from multiple, closely spaced scanlines in the transmit beam field.

The signals from the sub-apertures can be delayed and summed to form a group of multiline received scanlines. Grating lobes which arise by reason of the periodicity of the sub-apertures and can contribute clutter to the final image are reduced by producing two or more differently steered signals from each sub-aperture (patch). The steering difference is kept small, within the beamwidth of the patch. By keeping the steering delay profile less than $\lambda/2$, significant grating lobes are kept out of the image field.

A simple 1D example illustrates these effects. Consider a sixty-four element 1D linear array with inter-element spacing (pitch) of $\lambda/2$. The array is divided into four patches of sixteen elements each. Two beams are steered to the left and right of a nominal direction on each patch. The steering angles are limited so that other lines or samples can be interpolated between these two received multilines. It is desirable for the multilines to be radially far enough apart to support the creation of interspaced interpolated lines, but close enough together so that RF interpolation will not form artifacts due to spatial undersampling.

For example, if the steering delays are limited to correspond to less than $\pm\lambda/8$, then the two steered beams from each patch will fall within approximately the −1 dB width of the nominal patch beampattern. Also, because the steering delay between the left and right multiline on any element is thus limited to $\lambda/4$, RF interpolated lines can be produced using a simple two tap interpolation filter ($\lambda/2$ delays would correspond to the Nyquist criterion). The $\lambda/8$ delay limitation limits the steering angle to approximately $\pm(\lambda/8)/(4*\lambda)$ or $\frac{1}{32}$ radians. Thus the angle between the left and right multilines can be about $\frac{1}{16}$ radians, or about 3.6 degrees. If two other lines are symmetrically interpolated between the two received multilines, the resulting line spacing is approximately 1.2 degrees. A greater number of more closely spaced multilines or interpolated lines can also be produced as desired.

In the 1D array example, instead of producing a single scanline from each patch steered in the nominal steering direction, two scanlines are produced, one steered slightly left of the nominal steering direction and one steered slightly right. In the case of a 2D array, several variations are possible. For a rectilinear 2D array, four scanlines are produced for each patch, steered left, right, up and down in quadrature relationship. For a triangular-based 2D array such as a hexagonal array, three scanlines are produced at rotations of 120° as shown in FIG. 10d. The scanlines produced in this drawing are identified as $B_{\phi 0}$, $B_{\phi 120}$ and $B_{\phi 240}$, respectively, where the subscript number refers to the direction of rotation in the plane normal to the nominal steering direction of the patch and the angle $\phi$ is the small angle at which each scanline is tilted from the nominal steering direction. The angle $\phi$ is kept small as described above so that the three scanlines are kept within the beamwidth of the nominally steered beam. FIG. 10c illustrates a single scanline $B_0$ oriented normal to the patch 202, as would be produced by the system shown in FIG. 10a, which has a beam nominally steered normal to the face of the patch 202.

Although the foregoing examples suggest the use of a rectangular scan geometry for a rectilinear array and a triangular scan geometry for a hexagonal array, the scan geometry is not intrinsically linked to array geometry. A rectangular scan can be performed using a hexagonal array and vice versa.

A system operating as illustrated by FIG. 10d is shown in FIG. 10b. The scanhead in this drawing includes a 12 element patch micro-beamformer 350 which produces three multiline signals from each patch ($B_{\phi 0}$, $B_{\phi 120}$ and $B_{\phi 240}$, for example) instead of one line as did the micro-beamformer 280 of FIG. 10a. The micro-beamformed patch multilines are sent over the n conductors of a cable 351 to the ultrasound system's multiline beamformer 352. The multiline scanlines from all of the patches are combined in the system multiline beamformer 352 to form multiple scanlines. It is also possible to perform RF interpolation between the multiline scanlines.

However, rather than combine (beamform) the multiline signals from each patch and then perform RF interpolation on the beamformed signals, it is preferred that RF interpolation is performed on signals received from each patch separately prior to beamforming combination. In this case, prior to the weighting and summation operations of RF interpolation, each patch signal for each nominal steering direction is slightly delayed or advanced by an amount determined by each patch position and the offset of the interpolated line from the nominal line. The effect of the delays is to maximize the coherence of the patch waveforms combined in the RF interpolation step. This reduces interpolation errors and improves sensitivity. Specifically, if N interpolated lines are produced from M patches, each patch having K multilines, then MN RF interpolators are required with each interpolator preceded by K delay states, one for each multiline.

This same approach (i.e., delay+individual patch RF interpolation prior to patch signal combination) can also be used on patch signals received from different directions in a non-multiline mode provided that target motion between successive transmits is not excessive. The multiple scanlines are then processed by the image processor 284 and displayed on the display 100 as described previously. The number n of receive signal conductors of the cable is 768 if three multilines from each of 256 patches are sent simultaneously without multiplexing, a number which can be reduced by multiplexing if desired.

The patch multilines received by the ultrasound system can be interpolated to form additional scanlines prior to system beamformation if desired. However, since the processing of interpolation (weighting and summing) is mathematically compatible with that of beamformation, the patch multilines can be supplied directly to the system beamformer for formation of beamformed multilines.

Several display formats are known for the three-dimensional display. FIG. 12 shows a volumetric region 300 which is being scanned by a 2D transducer array 200. The volumetric region scanned can be in any desired shape, such as square, cylindrical, or pyramidal, depending upon the steering of the beams from the transducer. In this example, the volumetric region 300 is shown as a hexagonal pyramid. Shown within the volumetric region 300 is an image plane 302, which is delineated by the double lines. The image plane 302 is scanned in a time interleaved manner as the volumetric region 300 is scanned.

Time interleaving enables the echo data from the image plane 302 to be fully acquired in less time than that required to scan the full volumetric region 300 and the frame rate of display of the image plane 302 is thus greater than that of the volumetric display.

FIG. 13 shows a sequence $E_{300}$ during which echo data is acquired for the volumetric display. This sequence is periodically interrupted during which echo data $E_{302}$ for the planar display is acquired. Some of the planar echo data can be used for both displays. The relative durations of the sequences and the number of transmit-receive cycles needed for each display determine the frame rate relationship of the two displays.

For that matter, frame rate and scan time are significant factors effecting 3D imaging and 2D transducer arrays in general, and of course are interrelated. If you shorten scan time, you can improve processing time and frame rate. So minimizing scan time, or volume scanned would be an ideal way to improve processing time and frame rate, a desired goal of any type of 3D imaging.

SUMMARY OF THE INVENTION

According to one embodiment, a flexible geometry method for real-time ultrasound volume imaging is provided to decrease scan time and increase frame rate for imaging 3D volumes using 2D array-based transducers. In another embodiment, a flexible geometry method for real-time ultrasound volume imaging is provided to avoid scanning volumetric regions which have little or no value to the image of the overall volume. In a further embodiment, a flexible geometry method for real-time ultrasound volume imaging is provided to increase an overall or effective volume (or frame) rate of real-time volume acquisition by up to about 25%.

The flexible geometry method according to an embodiment of the present disclosure is achieved by firing a sub-set of the volume (i.e. firing only necessary beams and beams of necessary depths to cover the imaging volume of the desired geometry corresponding to the sub-set of the volumes), for example, using a circular- or elliptical-shaped beam pattern (i.e., the sub-set of the volume corresponding to an imaging volume of the desired geometry having a circular or elliptical cross-section), which may result in a beam pattern of about 21% fewer beams or less, with a commensurate time reduction. Such a 21% time savings translates in a 27% gain for volume frame rate. To do so, the scan is directed to acquire only that portion or subset of square or rectangular regions which are of specific importance, which in most cases is includes the central circular or elliptical portions (i.e., corresponding to the imaging volume of the flexible geometry). By limiting the scanning to such circular or elliptical regions (i.e., corresponding to circular or elliptical regions of the imaging volume of the flexible geometry), the corner portions, of limited importance, are ignored and the volume rate as well as the image quality is improved. (Accordingly, with respect to efficiency and flexibility, a maximal efficiency on volumetric imaging is achieved by transmitting and receiving only the necessary beams to various directions within the 3D volume of different geometries.)

What is of particular importance is that the sub-set of the original or full beam pattern may be any shape, size and orientation (i.e., wherein the sub-set of the original or full beam pattern corresponds to a subset of an original volume, the subset of the original volume corresponding to an imaging volume of the desired flexible geometry having a desired cross-section), where the flexible geometry system exhibits the flexibility to implement such variety of combinations (i.e., corresponding to firing only necessary beams and beams of necessary depth to cover the imaging volume of the desired flexible geometry). For that matter, the flexible geometry of the beam pattern may be in either a main volume or sub-volume, where the sub-set is therefore a sub-set of the main volume or a sub-set of the sub-volume (e.g., color Doppler within a B-mode volume). Further, the invention foresees implementation in those applications in multiple sub-volumes where one volume, such as B-mode, may overlap with other volumes, such as color.

The circular and elliptical definitions are just two implementations of the flexible nature enabled by the invention, wherein the invention is not limited to these implementations. In addition, the flexible geometry may be used in any possible 3D mode in which a particular system may be capable of implementing, as well as single volume (fundamental and/or harmonic) and multiple volumes (such as Doppler, flow and power).

BRIEF DESCRIPTION OF THE DRAWING FIGURES

DETAILED DESCRIPTION OF THE INVENTION

The physics of the speed of sound limits the number of scan lines which may be fired in a fixed unit of time such that the volume rate in real-time volume imaging is at times insufficient for B-made, color Doppler, and other volume imaging modes. Volume imaging using conventional two-dimensional (2D) array-based transducers uses square or rectangular shaped beam patterns to generate a pyramidal volume with either the same length on all 4 sides or the same length on two sides.

Figure 1:
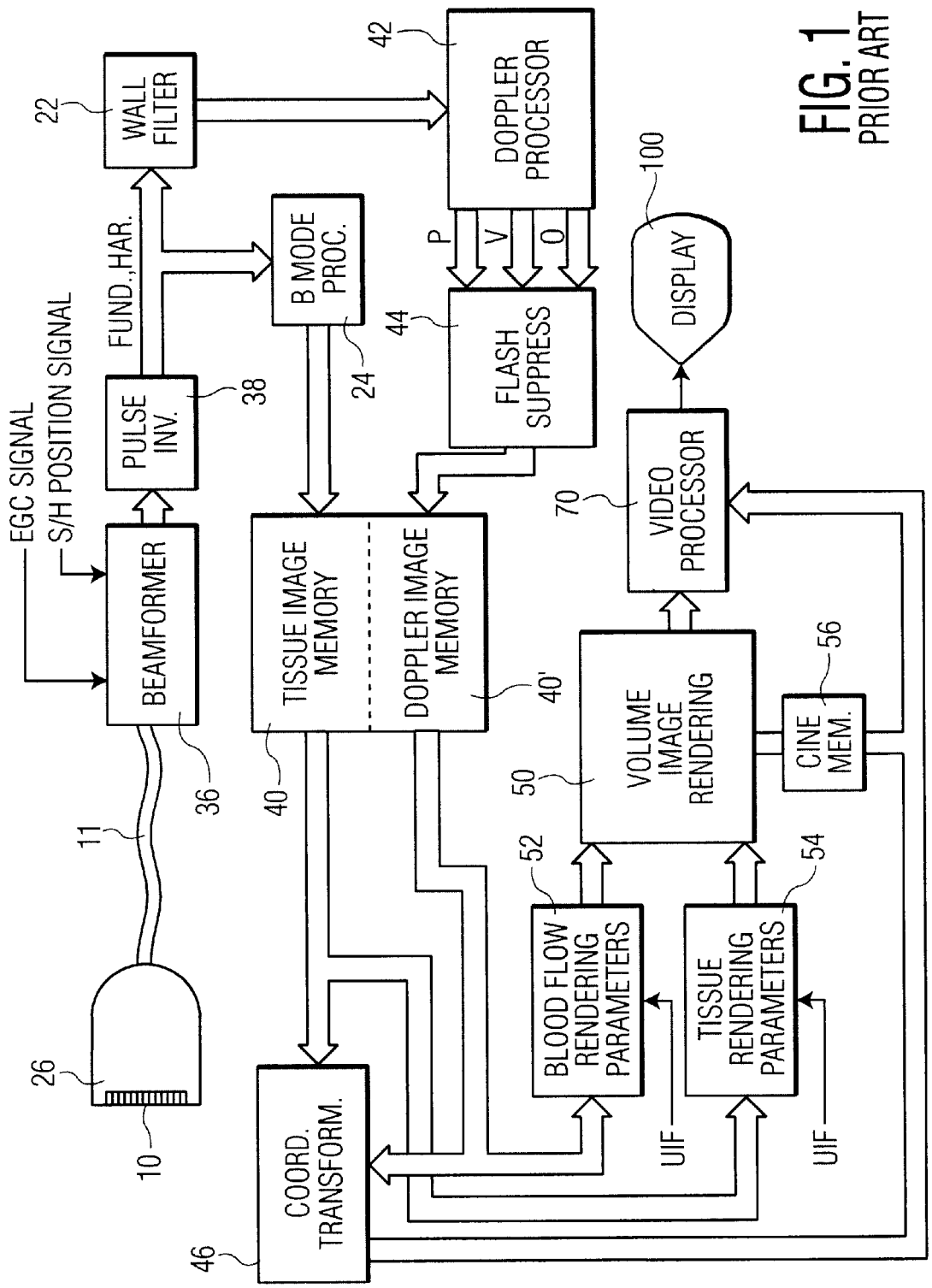
FIG. 1 illustrates a conventional ultrasonic diagnostic imaging system (PRIOR ART)
Figure 2:
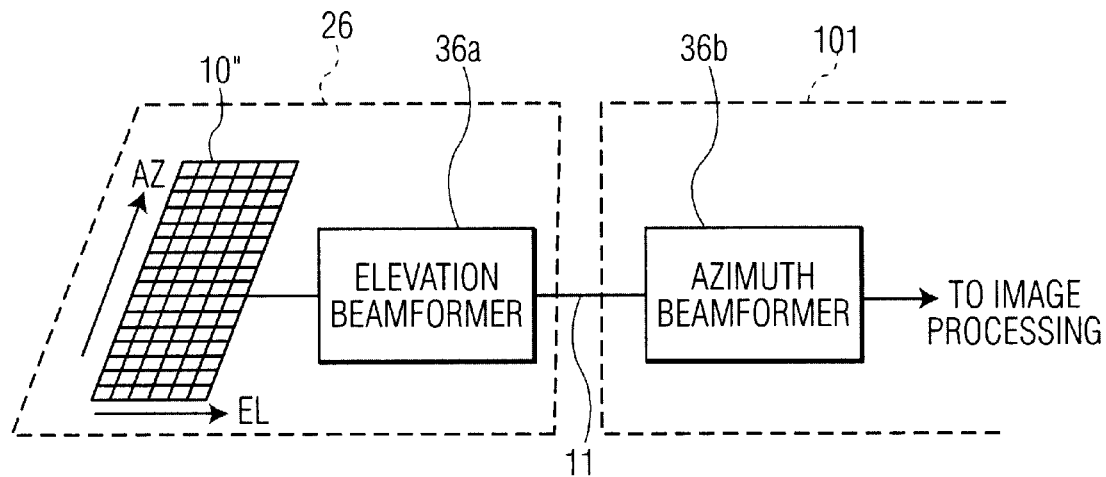
FIG. 2 illustrates the partitioning of beamforming between a scanhead and an ultrasound system (PRIOR ART)
Figure 3A:
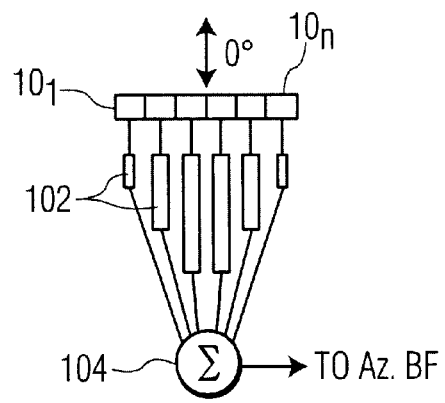
FIGS. 3a and 3b illustrate the steering of a beam in the elevation direction by a scanhead beamformer (PRIOR ART)
Figure 3B:
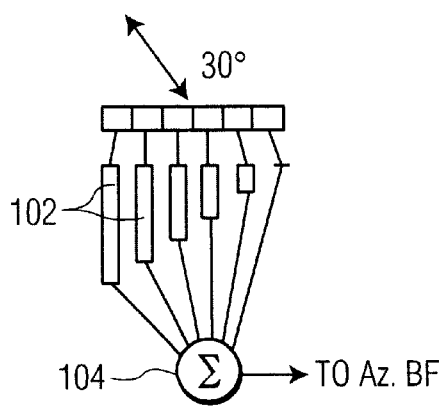
Figure 4A:
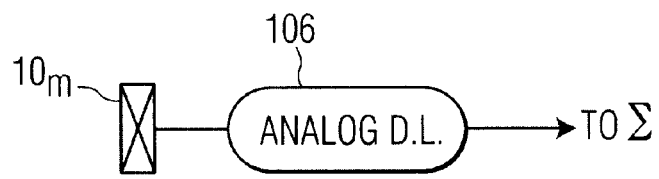
FIGS. 4a, 4b and 4c illustrate different embodiments of a scanhead elevation beamformer (PRIOR ART)
Figure 4B:
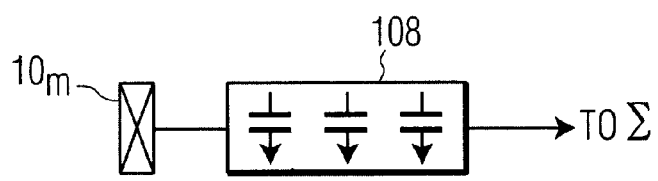
Figure 4C:
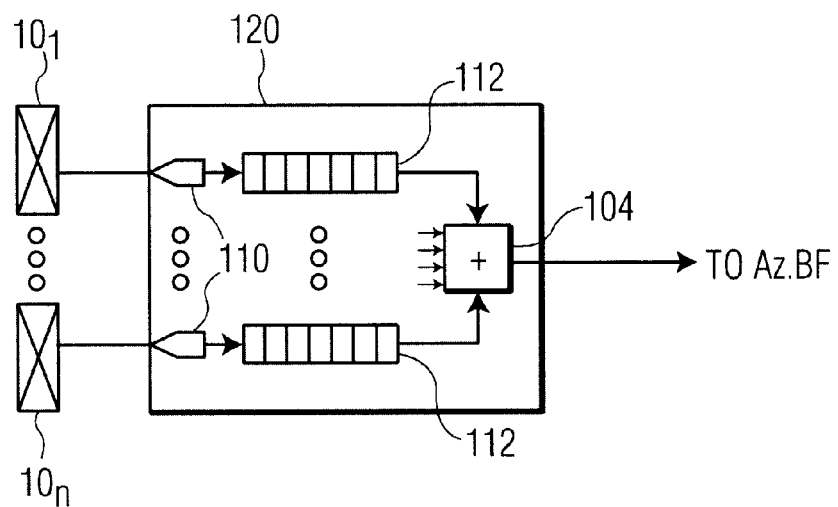
Figure 5:
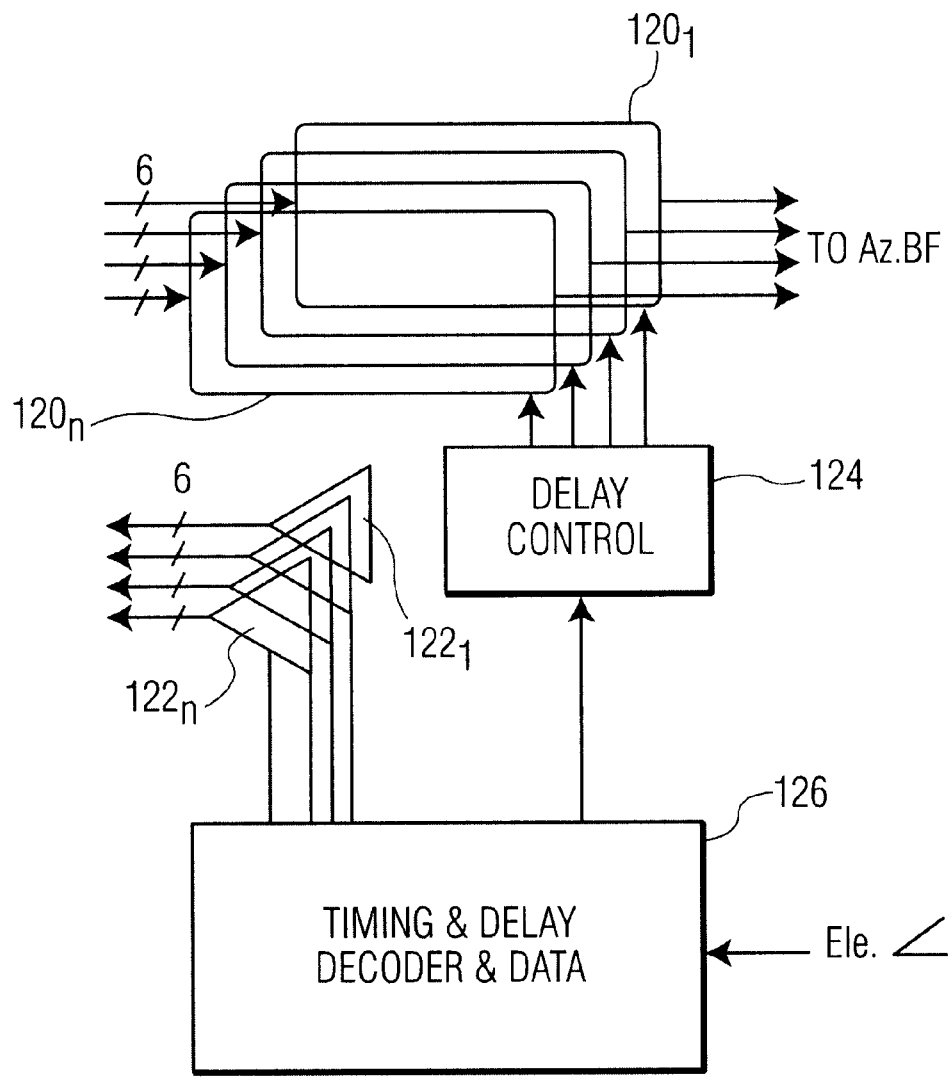
FIG. 5 illustrates an azimuth beamformer which operates with the elevation beamformers of FIGS. 4a, 4b, and 4c (PRIOR ART)
Figure 6:
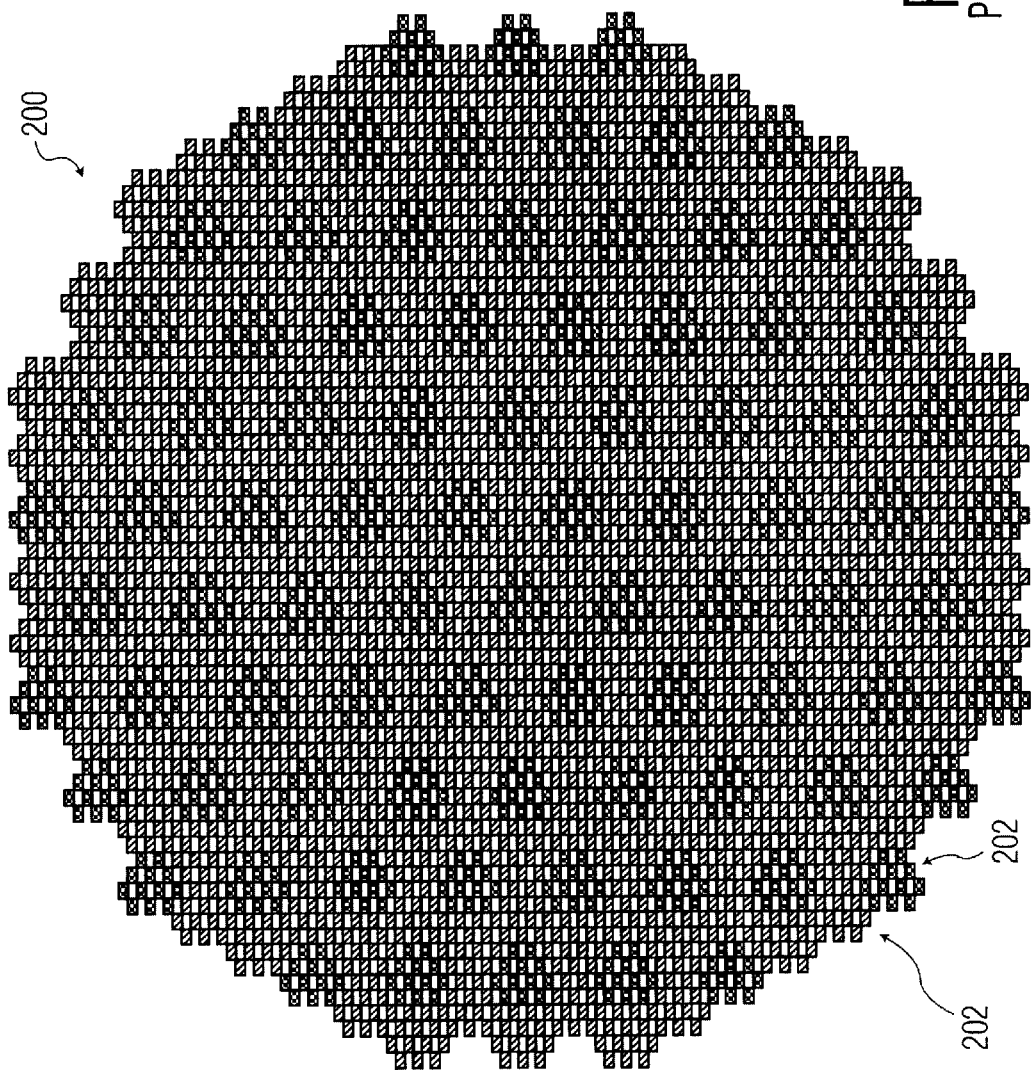
FIG. 6 is a plan view of a two dimensional transducer array for three-dimensional scanning in accordance with the present invention (PRIOR ART)
Figure 7:
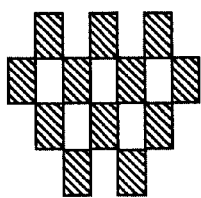
FIG. 7 illustrates a receive sub-aperture of the transducer array of FIG. 6 (PRIOR ART)
Figure 8A:
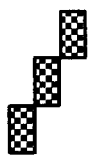
FIGS. 8a–8g illustrate different transmit sub-apertures of the transducer array of FIG. 6 (PRIOR ART)
Figure 8B:
Figure 8C:
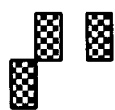
Figure 8D:
Figure 8E:
Figure 8F:
Figure 8G:
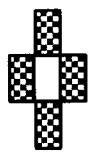
Figure 9:
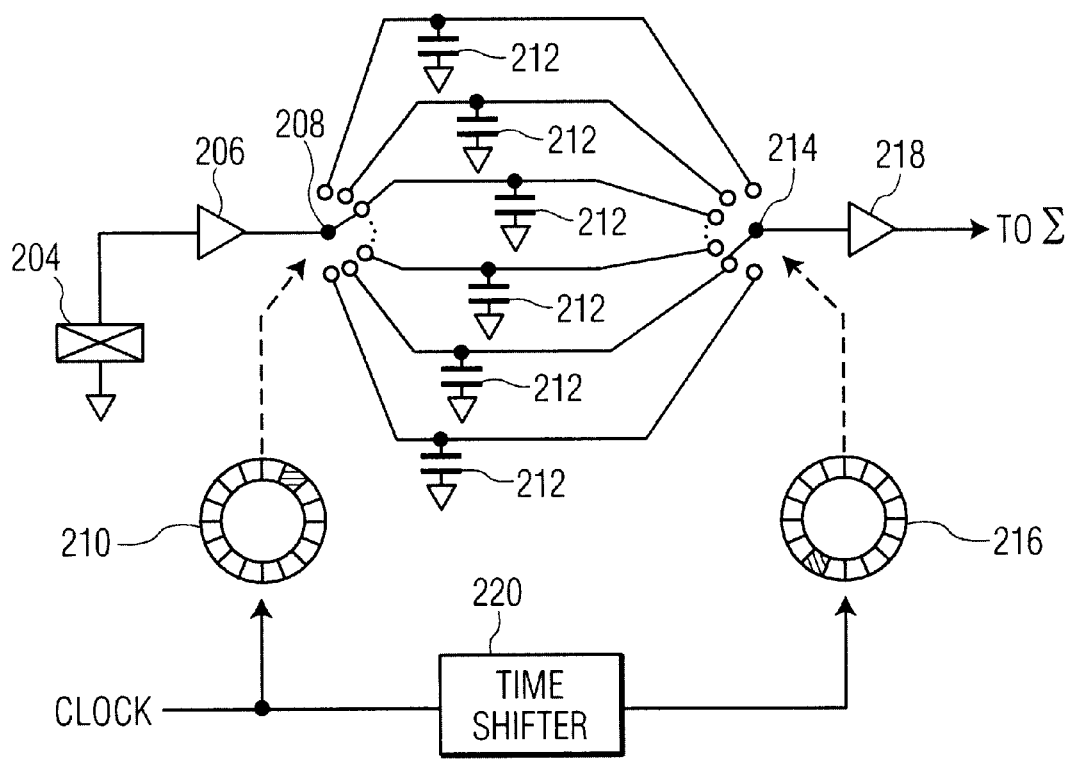
FIG. 9 illustrates scanhead microcircuitry for sampling the signals received by a transducer element of the transducer array of FIG. 6 in a desired time relationship (PRIOR ART)
Figure 10A:
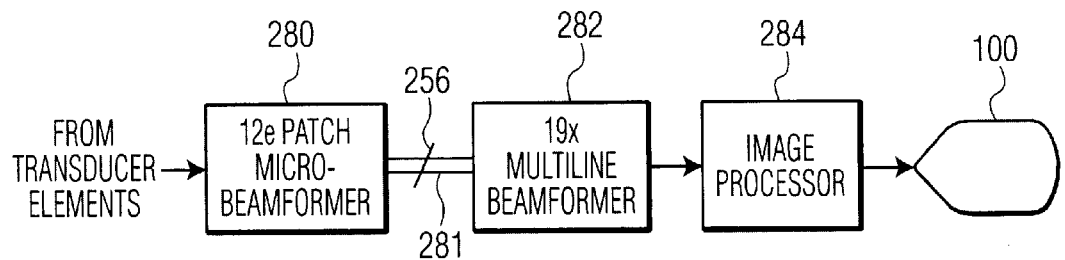
FIG. 10a illustrates a scanhead micro-beamformer and multiline beamformer system suitable for processing the signals received by the transducer array of FIG. 6 (PRIOR ART)
Figure 10B:
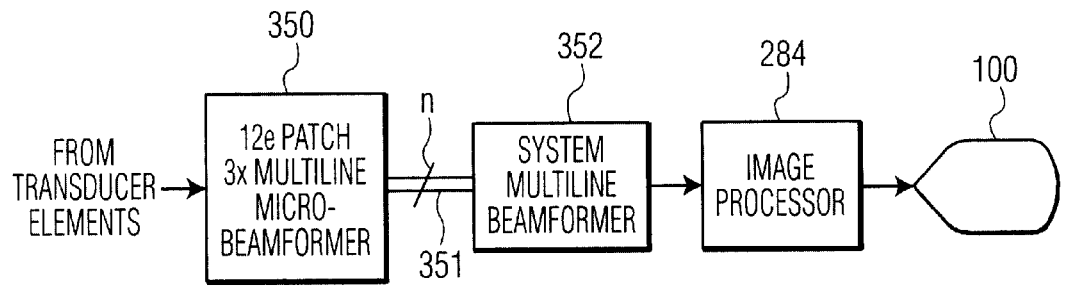
FIG. 10b illustrates the use of a multiline scanhead micro-beamformer in combination with a system multiline beamformer (PRIOR ART)
Figure 10C:
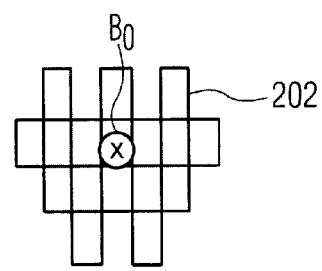
FIGS. 10c and 10d illustrate single line and multiline beam steering from a 2D transducer array patch (PRIOR ART)
Figure 10D:
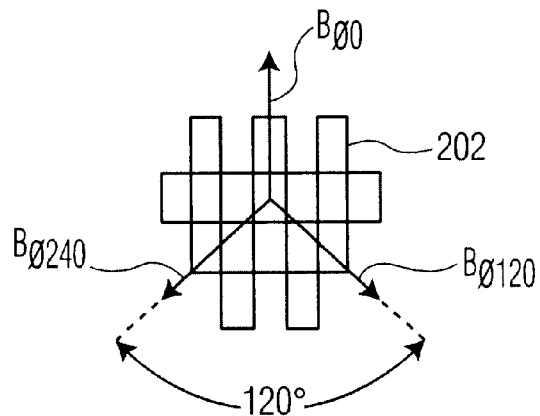
Figure 11A:
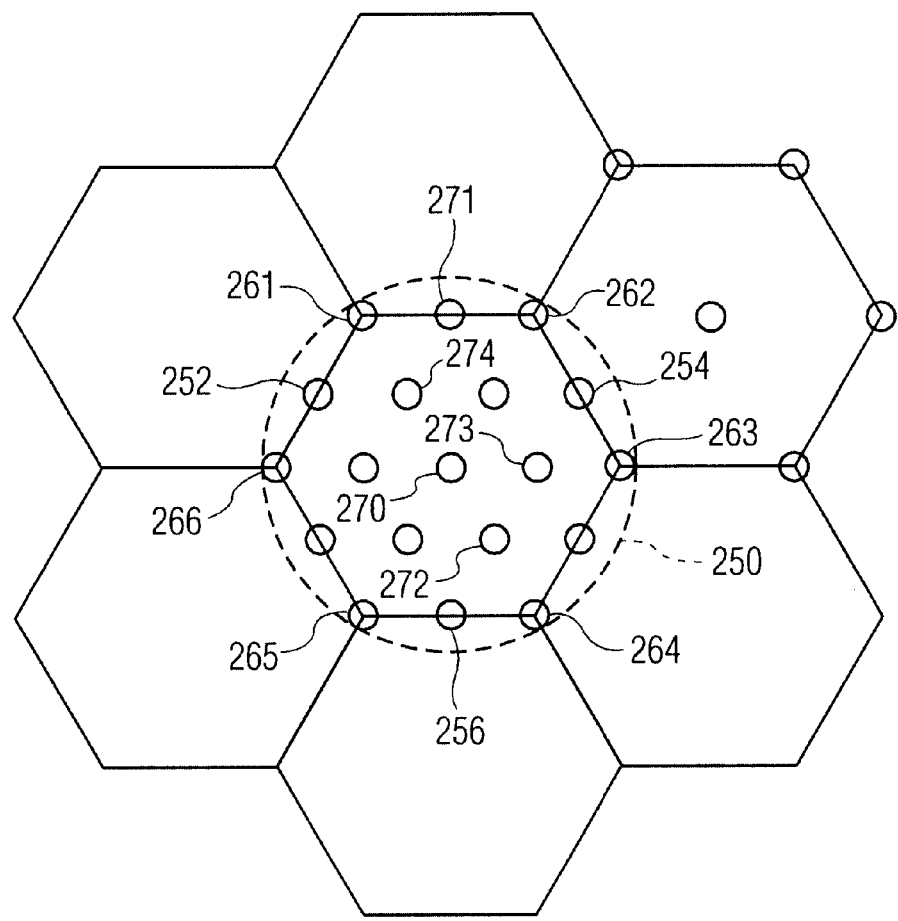
FIG. 11a illustrates operation of the system of FIG. 10a for a hexagonal scanning pattern (PRIOR ART)
Figure 11B:
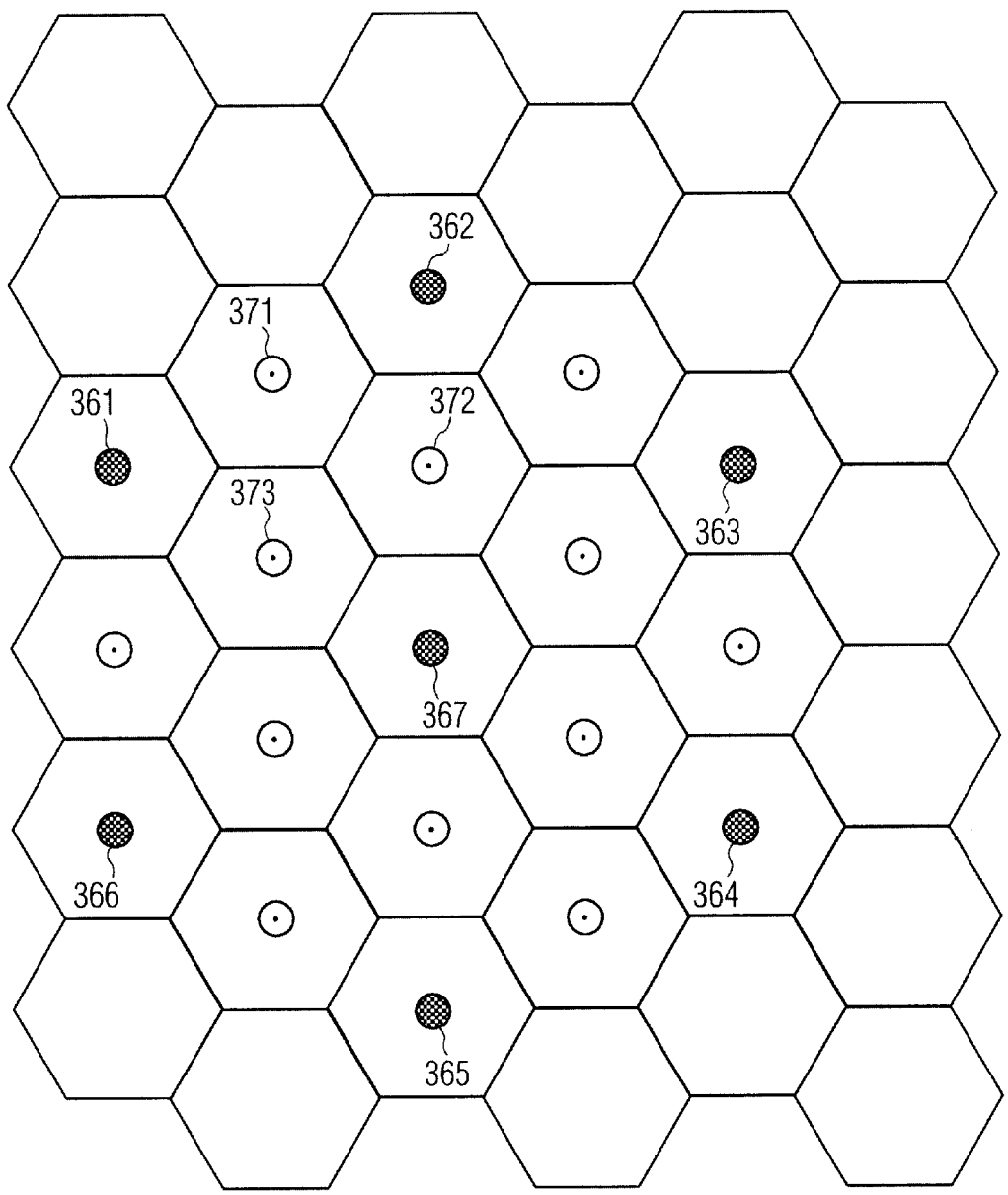
FIGS. 11b and 11c illustrate the use of interpolation to develop a hexagonal scanline pattern (PRIOR ART)
Figure 11C:
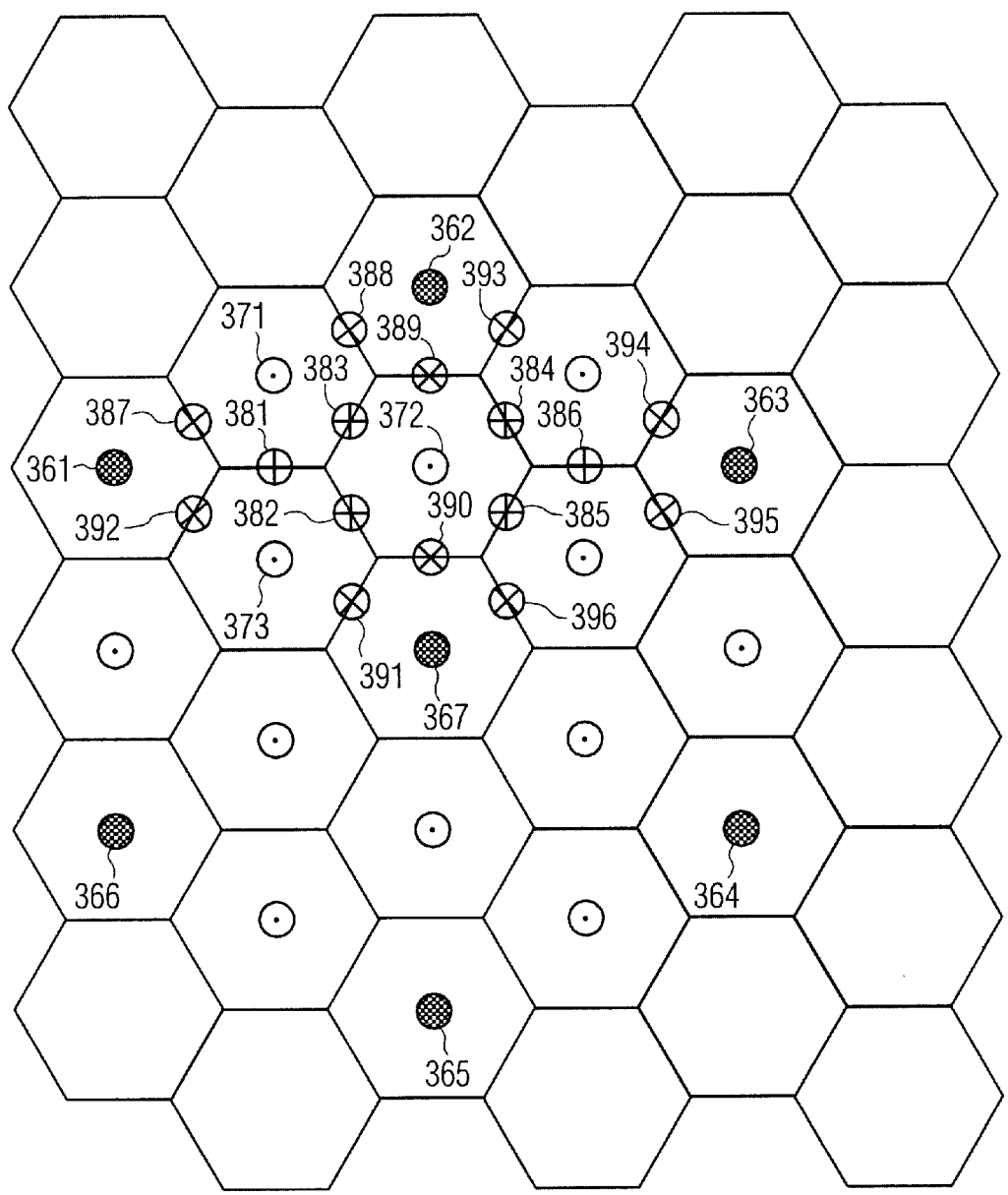
Figure 12:
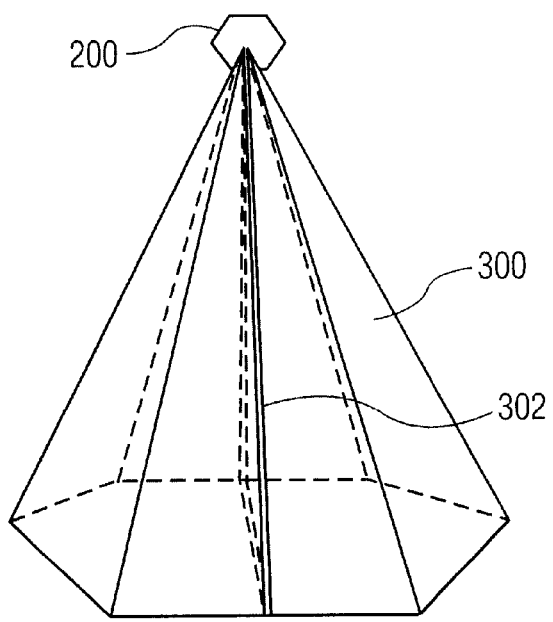
FIG. 12 illustrates a three-dimensional volume containing a two dimensional image plane (PRIOR ART)
Figure 13:
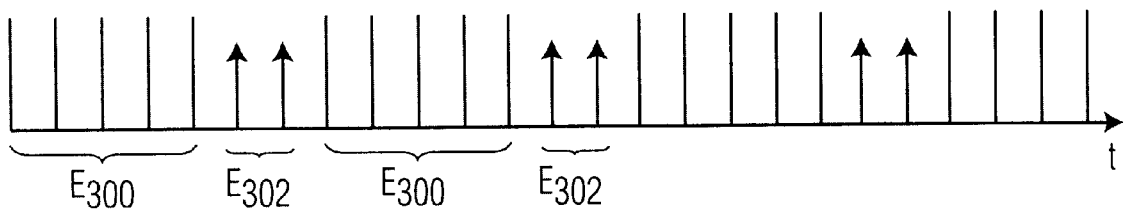
FIG. 13 illustrates the time interleaved sampling of the three-dimensional volume and two dimensional image plane of FIG. 12 (PRIOR ART)
Figure 14A:
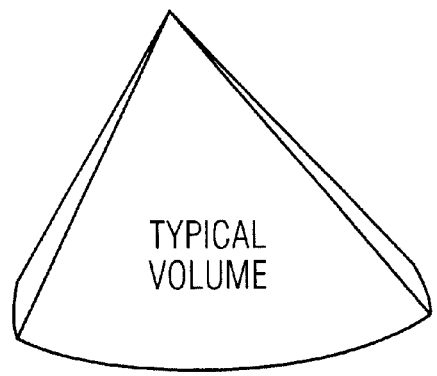
FIGS. 14a and 14b show the transducer geometry and scan pattern used in the prior art which is addressed by the present invention.
Figure 14B:
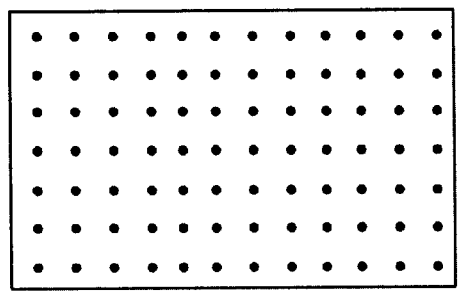

FIGS. 14a, 14b show a conventional 4 sided pyramidal volume scanned with a conventional 2D array transducer, respectively. Most 3D volume scanning, before the instant invention, was implemented using such transducer arrays. Such arrays, however, as mentioned above, do not take advantage of the fact that the important parts of volumes to be imaged are more central than peripheral. That is, the most desirous feature of a volume sits in the center, and not the edges, so that the volumetric portions associated at corners of a 4 sided or pyramidal volume are trivial. And scanning the corners of a volume takes time. Moreover, because of the steepness of the angle relative the normal to the plane, at the image edges, the quality there is less than that quality of image derived more centrally.

Figure 14C:
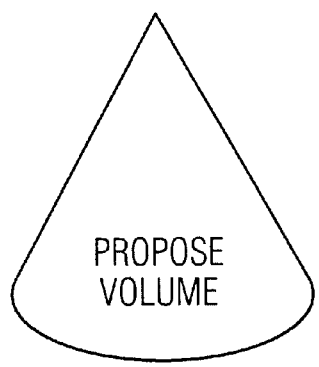
FIGS. 14c and 14d show one embodiment of the transducer geometry and the scan pattern which may be implemented in accordance with this invention.
Figure 14D:
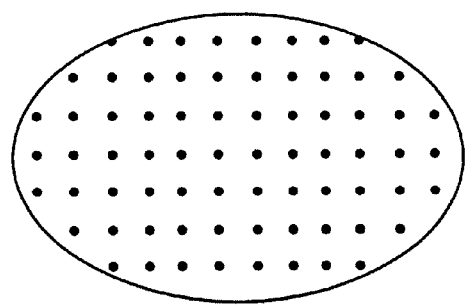

The present invention generates the firing pattern of any desirable shape and size, for example, using a conventional 2D array, to the elliptical pattern shown in FIG. 14d (the pattern may well be circular as well) in order to achieve a corresponding shaped volume imaged such as that set forth in FIG. 14c. That is, only those array elements comprising the circular or elliptical shaped pattern are fired, emanating from an area about 20 or 21% smaller than that rectangular area. The result is a 21 or so percent decrease in the time needed to scan a square or rectangle with the same diameter of such an ellipse or circle, corresponding to a 27% gain in volume frame rate.

The benefit should be readily obvious, because a circular or elliptical scan field in most cases covers as much a needed region of interest as the square or rectangular region, The missing portion of the image on the corners because they are not central and the quality at the corners is degraded as a natural result of beam steering, Hence, reducing the corners improves both volume rate and image quality. For that matter, such a scheme may be applied to any shaped 2D array transducers, as well as to all operable modes for volume imaging. The present invention may also be used with any mode of real-time or gated imaging and any modification of beam firing such as interleave imaging or other high-order multilines, through software.

Figure 15A:
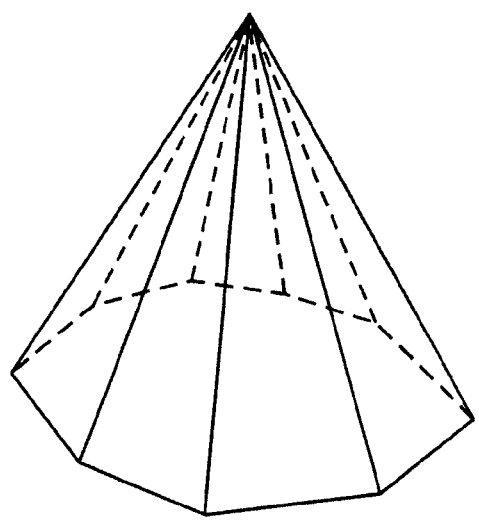
FIGS. 15a and 15b illustrate an N-sided beam pattern, where N is 8, in accordance with the invention.
Figure 15B:
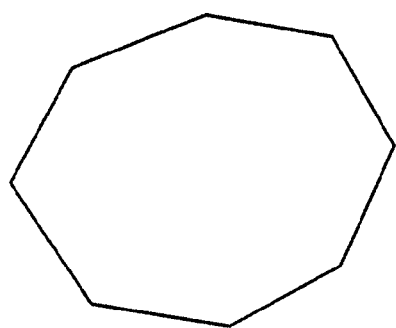

In a preferred embodiment, an octagonal array pattern and corresponding volume is shown (FIGS. 15a and 15b). The number of sides of a polygonal pattern and corresponding polygonal volume may be considered to be N for the purposes of this invention, where N is a positive integer value greater than 5 (and preferably 8 as shown in FIGS. 15a and 15b). As N gets large, for example, larger than 12 or 16, the N sided pattern and corresponding N-sided pyramidal volume begins to approach that of a circular or elliptical shape. A second preferred embodiment is where N is 10, a third preferred embodiment is where N is 12. Please note, however, that the number of sides is limited only by practicality.

What is claimed is:

1. A method for electronically scanning a volumetric region by means of a two dimensional array of transducer elements coupled to a beamformer, comprising:

actuating elements of the array according to a desired flexible geometry to transmit ultrasonic energy into the volumetric region, the desired flexible geometry corresponding to a sub-set of a volume of the volumetric region;

receiving echo signals by elements of the array in response to the transmitted ultrasonic energy; and forming beams in response to the echo signals that sample a sub-division of the volumetric region that comprises a sub-set of a beam pattern of the volumetric region, wherein limiting an arrangement of elements actuated, and the receiving of echo signals from the corresponding arrangement of elements actuated, flexibly steers the beams in one selected from the group consisting of a circular volumetric beam pattern and an elliptical volumetric beam pattern, when viewed axially.

2. The method of claim 1, wherein the step of forming includes steering the beams in a circular beam pattern when viewed axially for selecting the sub-set.

3. The method of claim 1, wherein the step of forming includes steering the beams in an elliptical beam pattern when viewed axially for selecting the sub-set.

4. The method of claim 1, wherein actuating comprises transmitting a transmit beam and wherein forming comprises producing a plurality of scanlines for every transmit beam.

5. The method of claim 4, wherein forming further comprises producing the plurality of scanlines in locations spatially arranged in a circular pattern.

6. The method of claim 4, wherein actuating requires that the two dimensional array is located in a scanhead and the receiving further comprises partially beamforming received echo signals by a micro-beamformer in the scanhead; and wherein the forming comprises producing a plurality of scanlines with a multiline beamformer located in an ultrasound system.

7. A three-dimensional ultrasonic diagnostic imaging system comprising:

a transducer including a two dimensional array of transducer elements which transmits beams of ultrasonic energy into a volumetric region and receives ultrasound signals in return, the array having an array geometry;

a beamformer coupled to the elements of the array and configured to spatially sample a sub-region of the volumetric region, said beamformer controls the transducer by limiting a firing of elements in the array geometry which correspond to the sub-region for generating a beam pattern, and further responsive to said beamformer limiting an arrangement of the elements actuated, and receiving echo signals from the corresponding arrangement of elements actuated, said beamformer flexibly steers the beams in the beam pattern, when viewing the beams axially, for causing the beam pattern to be shaped as a polygon volumetric beam pattern with N sides, where N is an integer number such that the beam pattern resembles one selected from the group consisting of a circular form and an elliptical form.

8. The three-dimensional ultrasonic diagnostic imaging system of claim 7, wherein N is large enough such that the beam pattern is a circular form.

9. The three-dimensional ultrasonic diagnostic imaging system of claim 7, wherein N is large enough such that the beam pattern is an elliptical form.

10. The three-dimensional ultrasonic diagnostic imaging system of claim 7, wherein the beamformer comprises a multiline beamformer which produces a plurality of scanlines for every transmit beam, and the volumetric region may be a sub-volume of a larger volumetric region.

11. The three-dimensional ultrasonic diagnostic imaging system of claim 10, further comprising a scanhead, wherein the scanhead includes a microbeamformer coupled to elements of the array which acts to partially beamform ultrasound signals received by the elements; and a cable which connects the scanhead to an ultrasound system, wherein the multiline beamformer is responsive to the partially beamformed ultrasound signals and is located in the ultrasound system.

12. The three-dimensional ultrasonic diagnostic imaging system of claim 11, wherein the ultrasound system further includes an interpolator responsive to the partially beamformed ultrasound signals which forms interpolated scanlines.

13. The three-dimensional ultrasonic diagnostic imaging system of claim 11, wherein elements of the array are grouped in octagonally shaped patches; and wherein the elements of each patch are coupled to a microbeamformer which acts to beamform signals received by the patch.

14. The three-dimensional ultrasonic diagnostic imaging system of claim 7, wherein the elements of the array are arranged in an elliptically packed pattern.

15. The three-dimensional ultrasonic diagnostic imaging system of claim 7, wherein the elements of the array are arranged in a circularly packed pattern.

16. The three-dimensional ultrasonic diagnostic imaging system of claim 7, wherein the system may be operated in at least one of single volume and multiple volume modes.

17. The three-dimensional ultrasonic diagnostic imaging system of claim 7, wherein the volumetric region may be a sub-volume of a larger volumetric region.

18. The three-dimensional ultrasound diagnostic imaging apparatus of claim 7, wherein the transducer is arranged to transmit in all modes of operation.

* * * * *